(12) United States Patent
Harding et al.

(10) Patent No.: US 11,511,082 B2
(45) Date of Patent: Nov. 29, 2022

(54) CATHETER HAVING A HARD DISTAL TIP

(71) Applicant: Becton, Dickinson and Company, Franklin Lakes, NJ (US)

(72) Inventors: Weston Harding, Lehi, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 522 days.

(21) Appl. No.: 15/957,382

(22) Filed: Apr. 19, 2018

(65) Prior Publication Data
US 2019/0321598 A1    Oct. 24, 2019

(51) Int. Cl.
*A61M 25/06* (2006.01)

(52) U.S. Cl.
CPC ...... *A61M 25/0606* (2013.01); *A61M 25/065* (2013.01); *A61M 25/0693* (2013.01)

(58) Field of Classification Search
None
See application file for complete search history.

(56) References Cited

U.S. PATENT DOCUMENTS

| | | | |
|---|---|---|---|
| 3,884,242 A * | 5/1975 | Bazell | A61M 16/04 128/207.15 |
| 5,489,269 A * | 2/1996 | Aldrich | A61B 17/3415 604/540 |
| 5,531,701 A | 7/1996 | Luther | |
| 5,533,988 A | 7/1996 | Dickerson et al. | |
| 6,440,119 B1 * | 8/2002 | Nakada | A61M 25/0014 604/500 |
| 6,890,321 B2 * | 5/2005 | Luther | A61M 25/0606 604/164.01 |
| 9,782,546 B2 * | 10/2017 | Woehr | A61M 25/0618 |
| 2003/0204169 A1 * | 10/2003 | Howell | B29C 48/13 264/209.3 |
| 2015/0231364 A1 | 8/2015 | Blanchard et al. | |
| 2017/0087338 A1 | 3/2017 | Belson | |
| 2017/0354799 A1 * | 12/2017 | Gupta | A61M 25/0606 |
| 2018/0093074 A1 | 4/2018 | Burkholz et al. | |

FOREIGN PATENT DOCUMENTS

WO    98/30259    7/1998

* cited by examiner

*Primary Examiner* — Manuel A Mendez
*Assistant Examiner* — Anh Bui
(74) *Attorney, Agent, or Firm* — Kirton McConkie; Whitney Blair; Kevin Stinger (57) ABSTRACT

A catheter assembly may include an over-the-needle catheter and introducer needle. The catheter may include a distal tip and an elongate tubular portion proximate the distal tip of the catheter. The distal tip may be constructed of a first material and may include at least a portion of a stepped surface. The tubular portion may be constructed of a second material having a harder durometer than the first material. The introducer needle may include a needle feature having another stepped surface configured to abut the stepped surface of the catheter when the introducer needle is in an insertion position such that proximal movement of the distal tip of the catheter relative to the introducer needle is inhibited.

12 Claims, 9 Drawing Sheets

CATHETER HAVING A HARD DISTAL TIP

BACKGROUND OF THE INVENTION

Intravenous (IV) catheters are commonly used for a variety of infusion therapies. For example, IV catheters may be used for infusing normal saline solution, various medicaments, or total parenteral nutrition into a patient. IV catheters may also be used for withdrawing blood from the patient.

A common type of IV catheter is an over-the-needle peripheral IV catheter. As its name implies, over-the-needle peripheral IV catheters may be mounted tightly over an introducer needle having a sharp distal tip. The introducer needle and the IV catheter are generally inserted at a shallow angle through the skin into vasculature of the patient with a bevel of the introducer needle facing away from the skin of the patient. During insertion, the sharp distal tip of the introducer needle may be distal to a distal end of the IV catheter. Thus, insertion of the IV catheter into the vasculature may follow piercing of the vasculature by the introducer needle.

Generally the introducer needle is constructed of metal, while the IV catheter may be constructed of a softer material, such as plastic, for example. Softer catheter materials as opposed to harder ones may be more comfortable for the patient, cause less irritation, and improve indwelling. However, if the IV catheter is too soft, its columnar strength may not be great enough to resist forces required to penetrate the skin and tissue of the patient.

In some instances, when the introducer needle and the IV catheter are inserted into the patient, there may be a tendency for the IV catheter to buckle, peel back, or move proximally away from the distal tip of the introducer needle. This may occur due to the skin or tissue of the patient pushing on a distal tip of the IV catheter during the insertion process. When the IV catheter peels back or moves proximally away from the distal tip of the introducer needle, the catheter may adopt have an enlarged cross-section, which may require greater insertion force, increased dilation at the insertion site, and/or increased pain for the patient.

It is to be understood that both the foregoing general description and the following detailed description are exemplary and explanatory and are not restrictive of the invention, as claimed.

BRIEF SUMMARY OF THE INVENTION

As used in the present disclosure, the term "distal" may refer to a portion of the catheter assembly, or component thereof, that is farther from a user. As used in the present disclosure, the term "proximal" may refer to a portion of the catheter assembly, or component thereof, that is closer to the user. As used in the present disclosure, the term "user" may refer to a clinician, doctor, nurse, or any other care provider and may include support personnel.

The present disclosure relates generally to catheter assembly for insertion into vasculature of a patient and related devices and methods. In some embodiments, the catheter assembly may include an over-the-needle catheter. In some embodiments, the catheter may include a distal tip constructed of a first material having a first durometer. In some embodiments, the catheter may include a first stepped surface, which may be annular. In some embodiments, the first stepped surface may include a rigid or semi-rigid first distal surface with a first uniform inner diameter, a first proximal surface with a second uniform inner diameter greater than the first uniform diameter, and a rigid or semi-rigid first transition surface disposed between the first distal surface and the first proximal surface. In some embodiments, at least the first distal surface and the first transition surface of the first stepped surface may be part of the distal tip of the catheter and thus constructed of the first material.

In some embodiments, the catheter may include an elongate tubular portion proximate and coupled to the distal tip of the catheter. In some embodiments, the tubular portion may be constructed of a second material. In some embodiments, a durometer of the first material may be harder than a durometer of the second material. In some embodiments, the distal tip of the catheter and the tubular portion may include a catheter lumen extending there through. In some embodiments, the first stepped surface may be disposed within the catheter lumen. In some embodiments, at least a portion of an outer surface of the distal tip may be tapered.

In some embodiments, the catheter assembly may include an introducer needle, which may include a needle feature having a second stepped surface, which may be annular. In some embodiments, the second stepped surface may include a second distal surface, a second proximal surface, and a second transition surface disposed between the second distal surface and the second proximal surface. In some embodiments, when the introducer needle is in an insertion position, the second distal surface may abut the first distal surface, the second proximal surface may abut the first proximal surface, and the second transition surface may abut the first transition surface such that proximal movement of the distal tip relative to the introducer needle is inhibited.

In some embodiments, the second proximal surface may be generally cylindrical. In some embodiments, the second proximal surface may include a notch, which may provide access to a needle lumen. In some embodiments, the second proximal surface may include at least a portion of a groove or flat portion. In some embodiments, the catheter assembly may include a flashback pathway disposed within the catheter lumen. In some embodiments, the flashback pathway may include the groove or flat portion.

In some embodiments, the groove may extend through the second transition surface and the second distal surface through a distal tip of the introducer needle. In some embodiments, the groove or flat portion may include the notch. In some embodiments, the notch may be disposed proximal to the second proximal surface. In some embodiments, the second proximal surface may extend through a proximal end of the catheter when the introducer needle is in the insertion position.

In some embodiments, the introducer needle may include a wall defining the needle lumen. In some embodiments, the second distal surface, the second transition surface, the second proximal surface, and the wall of the introducer needle may be monolithically formed as a single piece. In some embodiments, the needle feature may be bonded to the wall of the introducer needle to form the second transition surface and the second proximal surface.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION OF THE INVENTION

Figure 1A:
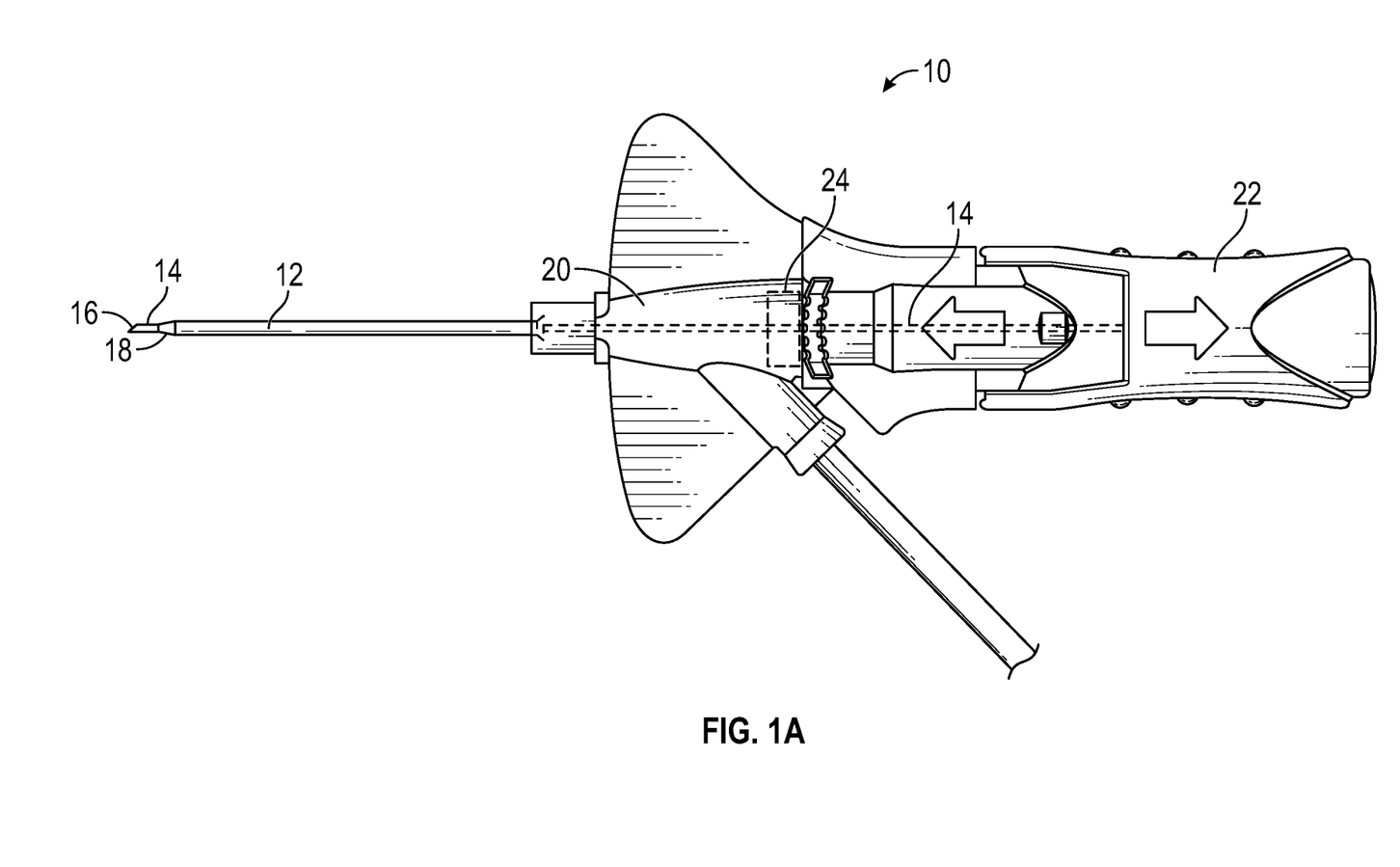
FIG. 1A is a top view of an example catheter assembly, according to some embodiments.

The present disclosure relates generally to catheter assembly for insertion into vasculature of a patient and related devices and methods. Referring now to FIG. 1A, in some embodiments, the catheter assembly 10 may include an over-the-needle catheter 12 and an introducer needle 14. FIG. 1A illustrates the introducer needle 14 in an insertion position for insertion into a patient. In some embodiments, when the introducer needle 14 is in the insertion position, a sharp distal tip 16 of the introducer needle 14 may be disposed beyond a distal tip 18 of the catheter 12.

In some embodiments, the catheter assembly 10 may include a catheter adapter 20. In some embodiments, a proximal end of the catheter 12 may be secured within the catheter adapter 20 and the catheter 12 may extend distally from the catheter adapter 20. In some embodiments, a proximal end of the introducer needle 14 may be secured within a needle hub 22 of the catheter assembly 10.

The catheter assembly 10 may include any type of catheter assembly having a catheter and introducer needle. Although the catheter assembly 10 illustrated in FIG. 1A is integrated having an integrated extension tube, it is understood that the catheter assembly 10 may be straight or non-integrated. Non-limiting examples of integrated IV catheter systems may include, for example, the BD NEXIVA™ Closed IV Catheter System, the BD NEXIVA™ DIFFUSICS™ Closed IV Catheter System, or the Becton Dickinson PEGASUS™ Safety Closed IV Catheter System. A non-limiting example of a straight or non-integrated catheter assembly is the BD INSYTE™ AUTOGUARD™ Shielded IV Catheter. In some embodiments, the catheter assembly 10 may include any variety of needle safety mechanism, which may shield the distal tip 16 of the introducer needle 14.

In some embodiments, the catheter assembly 10 may include any suitable type of blood control septum, which may be disposed within a lumen of the catheter adapter 20. FIG. 1A illustrates an example blood control septum 24, according to some embodiments. In some embodiments, the introducer needle 14 may be proximally withdrawn through the septum 24 after the catheter 12 is properly placed within the vasculature. In some embodiments, the septum 24 may be elastomeric. In some embodiments, the septum 24 may divide the lumen of the catheter adapter 20 into a proximal chamber and a distal chamber.

Figure 1B:
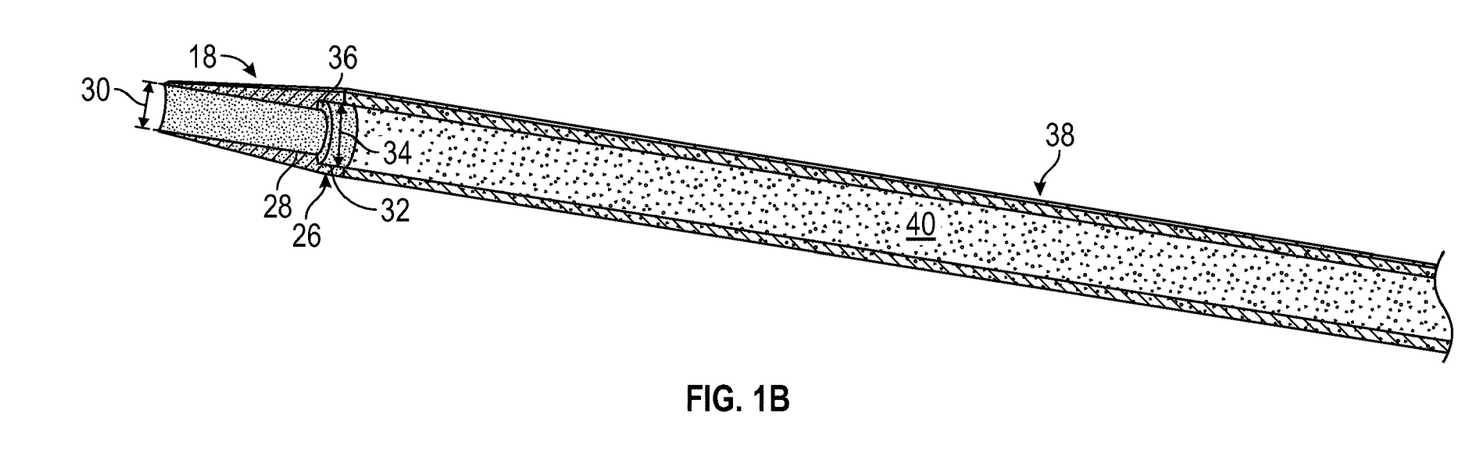
FIG. 1B is a cross-sectional view of a distal end of an example catheter of the catheter assembly of FIG. 1A, according to some embodiments.

Referring now to FIG. 1B, in some embodiments, the catheter 12 may include the distal tip 18, which may be constructed of the first material having a first durometer. In some embodiments, the first material may be rigid or semi-rigid. In some embodiments, the catheter 12 may include a first stepped surface 26, which may be annular. In some embodiments, the first stepped surface 26 may include a rigid or semi-rigid first distal surface 28 with a first uniform inner diameter 30, a first proximal surface 32 with a second uniform inner diameter 34 greater than the first uniform diameter 30, and a rigid or semi-rigid first transition surface 36 disposed between the first distal surface 28 and the first proximal surface 32.

In some embodiments, an entirety of the distal tip may be constructed of the first material. In some embodiments, at least the first distal surface 28 and the first transition surface 36 of the first stepped surface 26 may be part of the distal tip 18 of the catheter 12 and thus constructed of the first material. In some embodiments, the first distal surface 28, the first transition surface 36, and the first proximal surface 32 of the first stepped surface 26 may be part of the distal tip 18 and thus constructed of the first material.

In some embodiments, the catheter 12 may include an elongate tubular portion 38 proximate and coupled to the distal tip 18 of the catheter. In some embodiments, the tubular portion 38 may be constructed of a second material. In some embodiments, a durometer of the first material may be harder than a durometer of the second material. In some embodiments, the distal tip 18 and the tubular portion 38 may include a catheter lumen 40 extending there through. In some embodiments, the first stepped surface 26 may be disposed within the catheter lumen 40.

In some embodiments, the first material and/or the second material may include a composite material. In some embodiments, the first material may include one or more of the following: silicon, polyurethane, metal, plastic, and another suitable material. In some embodiments, the second material may one or more of the following: silicon, polyurethane, metal, plastic, and another suitable material. In some embodiments, the first material may include a first polyurethane, and the second material may include a second polyurethane. In some embodiments, the first material may include a first silicon, and the second material may include a second silicon. In some embodiments, the first material may include metal and/or the second material may include plastic. In some embodiments, the second material may include a flexible material.

In some embodiments, the second material may include a softer material than the first material, which may be more comfortable for the patient and result in fewer indwelling problems. In some embodiments, the softer second material may allow the catheter 12 to be inserted into the vasculature longer before complications arise. In some embodiments, the second stepped surface 44 may contact and support the first stepped surface 26 and the distal tip 16 when the introducer needle 14 is in the insertion position, such that proximal movement of the distal tip 16 relative to the introducer needle 14 is inhibited and compressive forces necessary for the distal tip 16 to penetrate the skin are transferred to the introducer needle 14, which may be constructed of metal. In some embodiments, the contact between the first stepped surface 26 and the second stepped surface 44 when the introducer needle 14 is in the insertion position may allow the second material to be even softer than a standard catheter body. In some embodiments, the second material may allow the tubular portion 38 to bend when the catheter adapter 20 is secured to the skin of the patient, while the first material may facilitate successful insertion of the catheter 12 into the vasculature.

In some embodiments, the first transition surface 36 may include a shoulder. In some embodiments, the first transition surface 36 may be disposed at about 90 degrees with respect to a longitudinal axis of the catheter assembly 10, as illustrated, for example, in FIG. 1B. In some embodiments, the first transition surface 36 may be disposed at an angle other than 90 degrees with respect to the longitudinal axis of the catheter assembly 10. In some embodiments, the first transition surface 36 may be smooth and/or planar. In some embodiments, the first transition surface 36 may be uneven, rough, or irregular. In some embodiments, the first transition surface 36 may be curved.

Figure 1C:
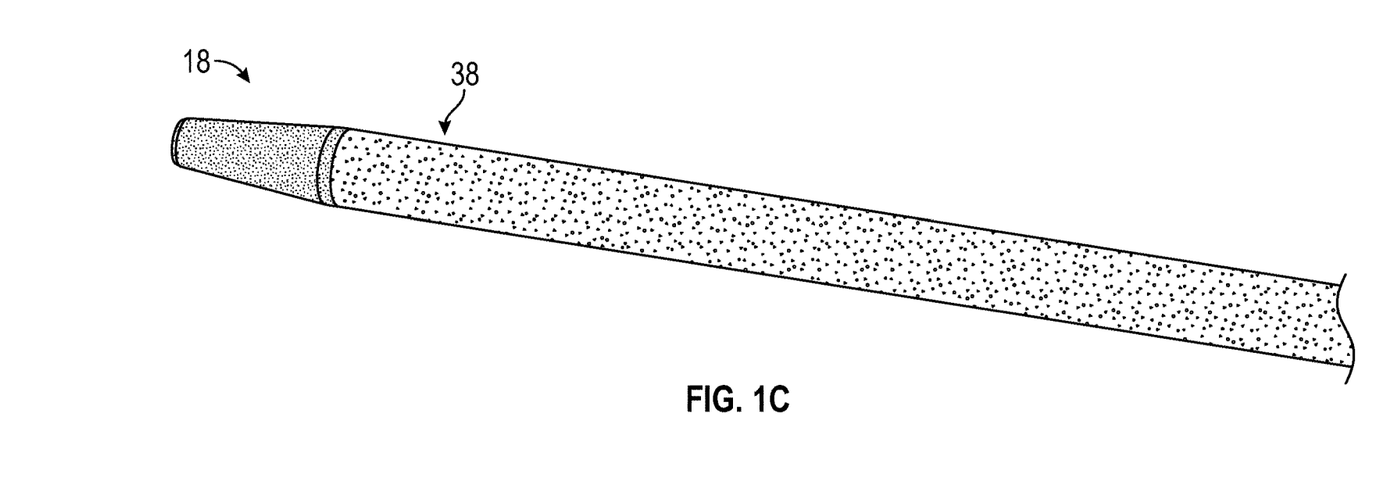
FIG. 1C is an upper perspective view of the distal end of the catheter of FIG. 1B, according to some embodiments.

Referring now to FIG. 1C, in some embodiments, at least a portion of an outer surface of the distal tip 18 may be tapered, which may facilitate entry of the catheter 12 into the skin and tissues of the patient behind the distal 16 tip of the introducer needle 14 as the distal tip 16 cuts a pathway.

Referring now to FIG. 2A-2D, in some embodiments, the catheter assembly 10 may include the introducer needle 14, which may include a needle feature 42. In some embodiments, the needle feature 42 may include a second stepped surface 44, which may be annular. In some embodiments, the second stepped surface 44 may include a second distal surface 46, a second proximal surface 48, and a second transition surface 50 disposed between the second distal surface 46 and the second proximal surface 50. In some embodiments, when the introducer needle 14 is in the insertion position, the second distal surface 46 may abut the first distal surface 28, the second proximal surface 48 may abut the first proximal surface 32, and the second transition surface 48 may abut the first transition surface 36 such that proximal movement of the distal tip 18 of the catheter 12 relative to the introducer needle 14 is inhibited.

In some embodiments, the second transition surface 50 may include a shoulder. In some embodiments, the second transition surface 50 may be disposed at about 90 degrees with respect to a longitudinal axis of the catheter assembly 10, as illustrated, for example, in FIG. 2B. In some embodiments, the second transition surface 50 may be disposed at an angle other than 90 degrees with respect to the longitudinal axis of the catheter assembly 10. In some embodiments, the second transition surface 50 may be smooth and/or planar. In some embodiments, the second transition surface 50 may be uneven, rough, or irregular. In some embodiments, the needle feature 42 may include a bump and/or the second transition surface 50 may be curved.

Figure 2A:
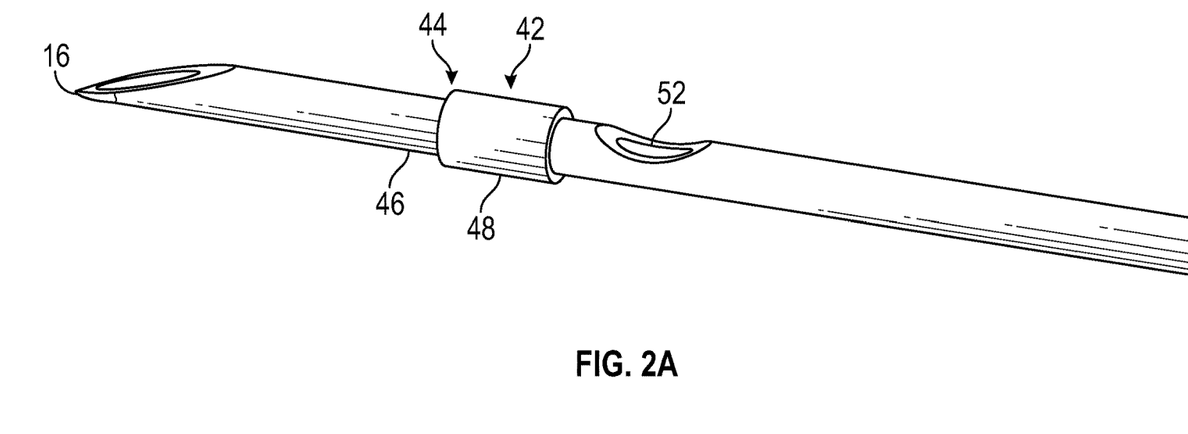
FIG. 2A is an upper perspective view of a distal end of an example introducer needle of the catheter system of FIG. 1A, according to some embodiments.
Figure 2B:
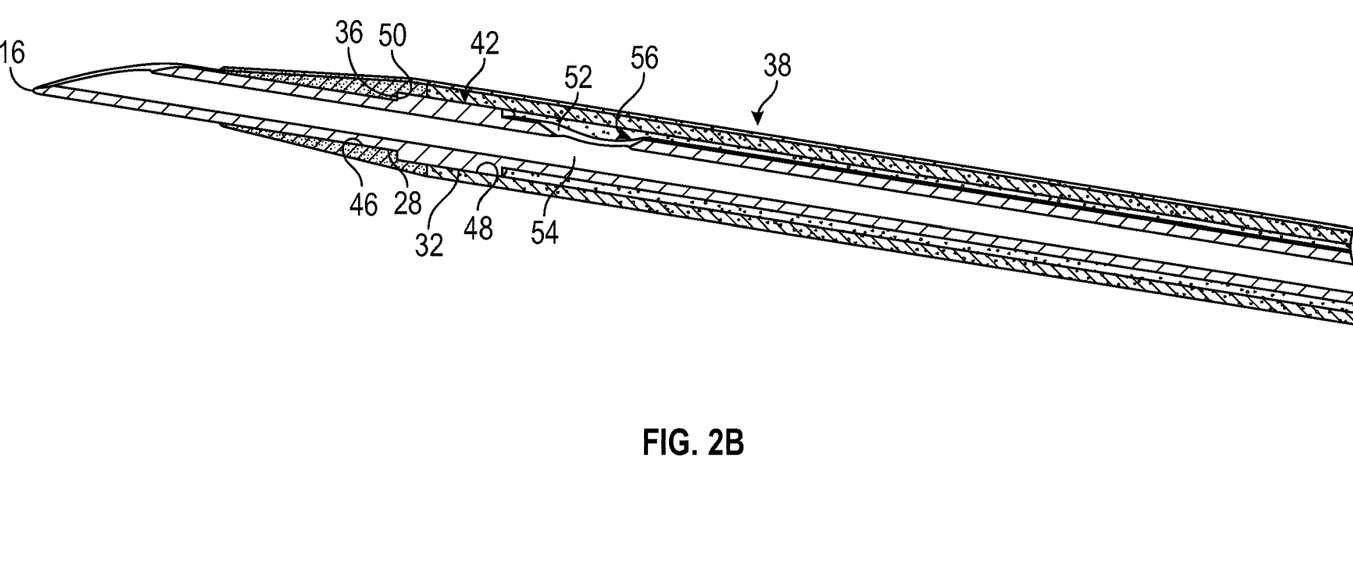
FIG. 2B is a cross-sectional view of the distal end of the introducer needle of FIG. 2A disposed in the insertion position within the catheter of FIG. 1B, according to some embodiments.
Figure 2C:
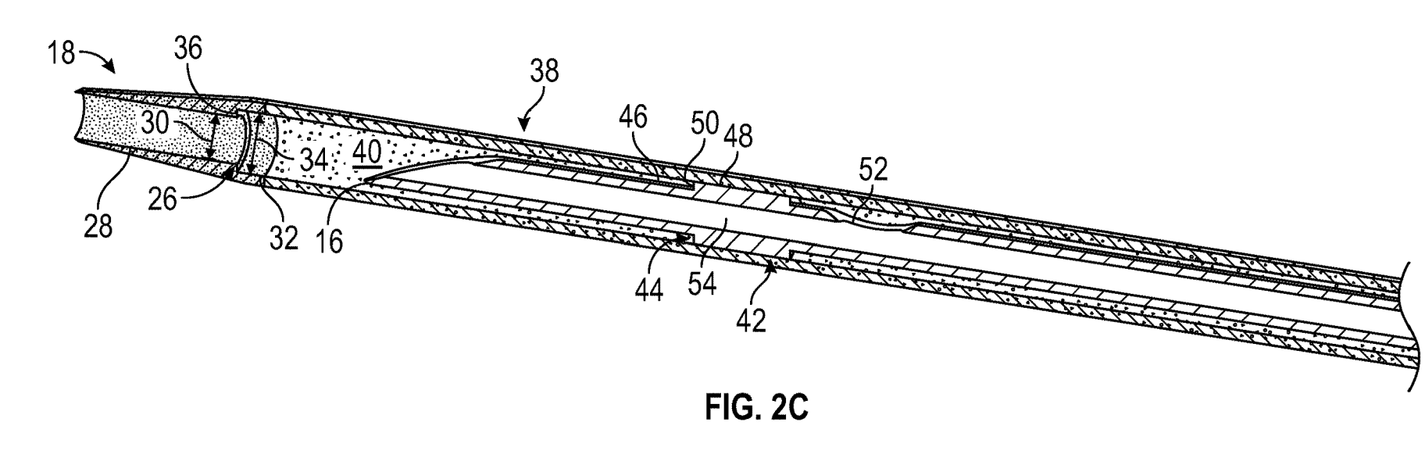
FIG. 2C is a cross-section view of the distal end of the introducer needle of FIG. 2A partially withdrawn from the catheter of FIG. 1B, according to some embodiments.

In some embodiments, the first stepped surface 26 may include a corresponding or mirror-image shape to the second stepped surface 44 such that there are no spaces between the first stepped surface 26 and the second stepped surface 44. In some embodiments, an outer diameter of the second proximal surface 48 may be greater than the first uniform inner diameter 30 of the catheter 12 such that the needle feature 42 is prevented from passing distally through the first distal surface 28. In some embodiments, the outer diameter of the second proximal surface 48 may be approximately equal to or slightly less than the second uniform inner diameter 34 such that the needle feature 42 is capable of sliding through the tubular portion 38 but still contacts an inner surface of the tubular portion 38 to provide support to the catheter 12. In some embodiments, an outer diameter of the second distal surface 46 may be approximately equal to or slightly less than the first uniform inner diameter 34 such that the first distal surface 28 may fit within and support the first distal surface 28.

Figure 2D:
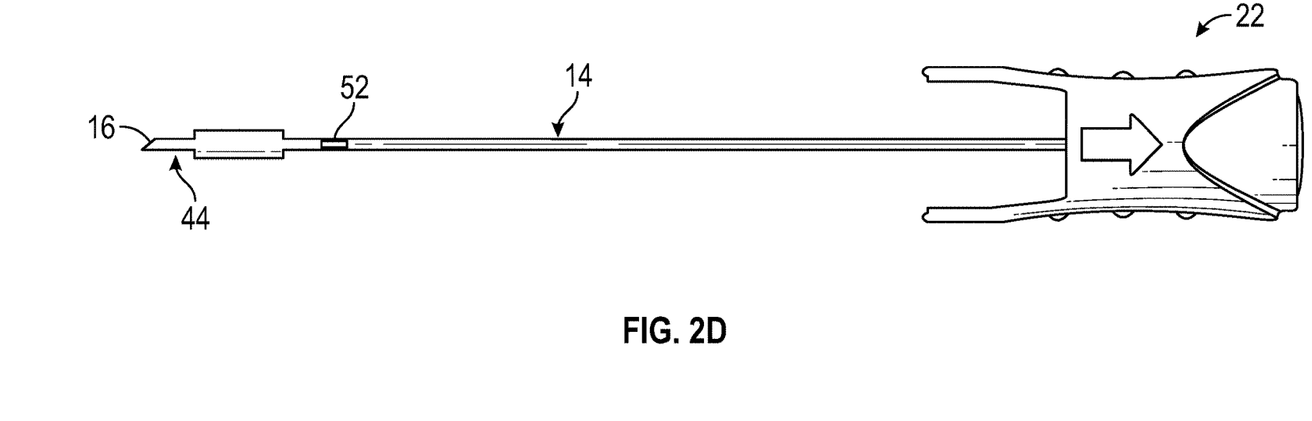
FIG. 2D is a top view of the introducer needle of FIG. 2A disposed within an example needle hub of the catheter system of FIG. 1A, according to some embodiments.

In some embodiments, the second proximal surface 48 may be generally cylindrical. In some embodiments, a notch 52 providing access to a needle lumen 54 may be disposed proximal to the second proximal surface. In some embodiments, a portion of the introducer needle 14 proximate the notch 52 may be spaced apart from an inner surface of the catheter 12 or tubular portion 38 to form a flashback pathway 56. In some embodiments, the second proximal surface may extend proximally to an opposing stepped surface, which may form a distal end of the flashback pathway 56, as illustrated, for example, in FIGS. 2B and 2D. In some embodiments, the flashback pathway 56 may be disposed within the catheter lumen 40 between an outer surface of the introducer needle 14 and an inner surface of the catheter 12. FIG. 2D illustrates the introducer needle 14 removed from the catheter adapter 20, according to some embodiments.

In order to verify proper placement of the introducer needle 14 and/or the catheter 12 in the vasculature, the user may generally confirms that there is flashback of blood, which may be visible to the user. In some embodiments, the catheter 12 and/or another portion of the catheter assembly 10 may be at least partially transparent to aid the user in viewing the flashback. In some embodiments, in response to the distal tip 16 of the introducer needle 14 being positioned within the vasculature, blood may flow proximally through the needle lumen 54, exit the needle lumen through the notch 52, and then travel proximally between an outer surface of the introducer needle 14 and an inner surface of the catheter 12. Accordingly, the user may visualize a small amount of blood "flashback" and thereby confirm placement of the catheter 12 within the vasculature. In some embodiments, once placement of the introducer needle 14 within the vasculature has been confirmed, the user may temporarily occlude flow in the vasculature and withdraw the introducer needle 14 from the vasculature, leaving the catheter 12 in place for future blood withdrawal and/or fluid infusion. In some embodiments, the catheter assembly 10 may be vented to allow flashback to occur.

In some embodiments, the introducer needle 14 may include a wall defining the needle lumen 54. In some embodiments, the second distal surface 46, the second transition surface 50, the second proximal surface 48, and the wall of the introducer needle 14 may be monolithically formed as a single piece. In some embodiments, the needle feature 42 may be bonded to the wall of the introducer needle 14 to form the second transition surface 50 and the second proximal surface 48. For example, the needle feature 42 may include metal, plastic, or another suitable material that is bonded to the wall of the introducer needle 14. In some embodiments, the needle feature 42 may be created by partially crimping the introducer needle 14. In some embodiments, the needle feature 42 may be formed by removing portions of the wall distal and/or proximal to the needle feature 42.

Figure 3A:
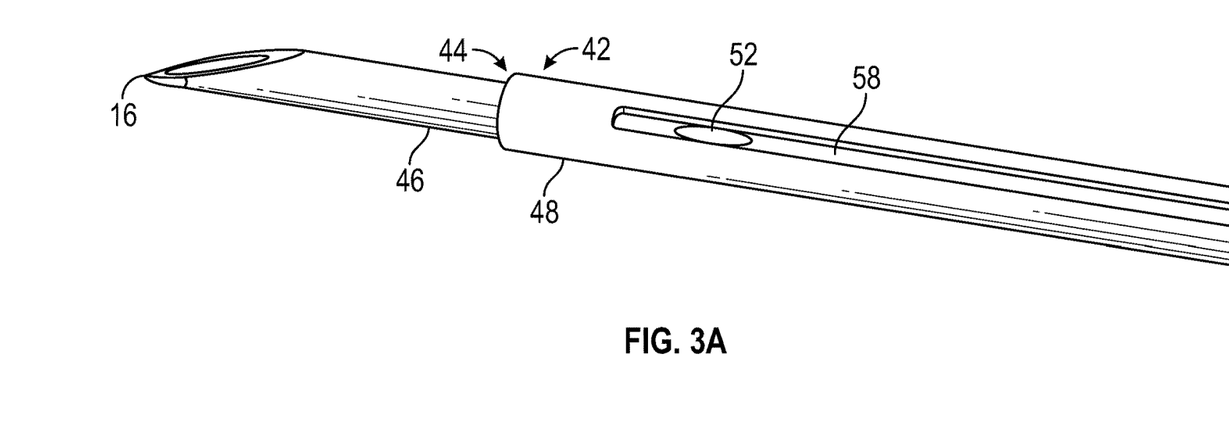
FIG. 3A is an upper perspective view of a distal end of another example introducer needle of the catheter system of FIG. 1A, according to some embodiments.
Figure 3B:
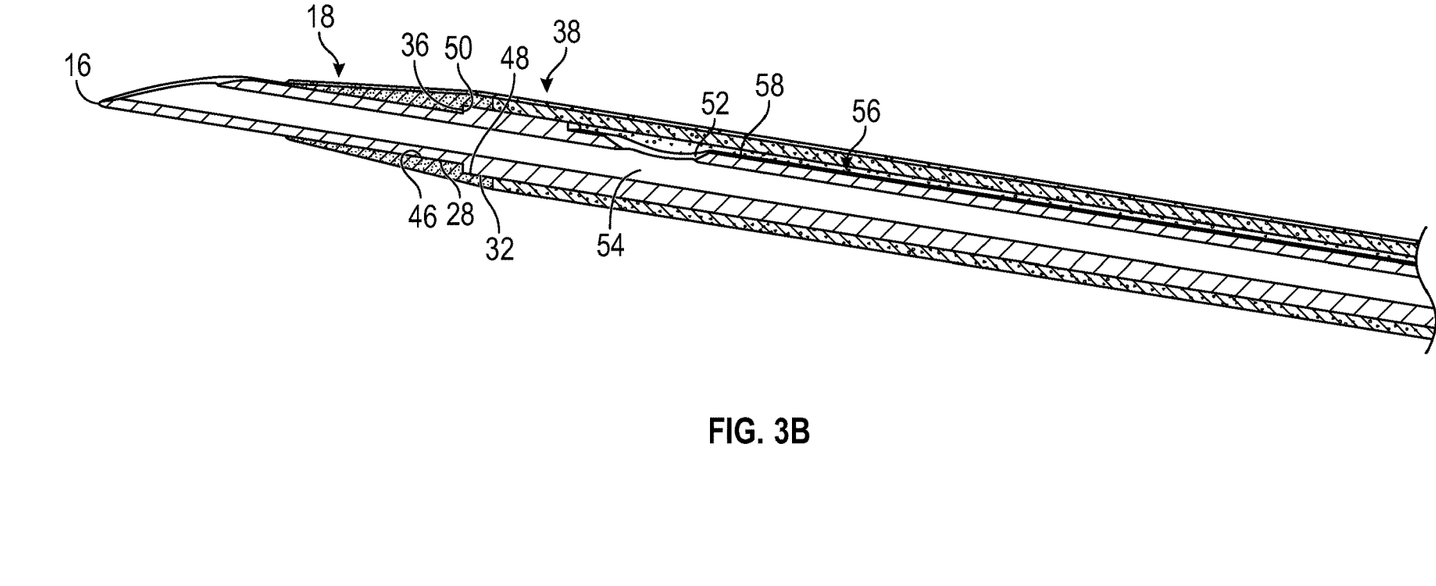
FIG. 3B is a cross-sectional view of the distal end of the introducer needle of FIG. 3A disposed in the insertion position within the catheter of FIG. 1B, according to some embodiments.

Referring now to FIGS. 3A-3B, in some embodiments, the second proximal surface 48 may include at least a portion of a flat portion or groove 58. An example flat portion 59 is illustrated in FIG. 3E, according to some embodiments. In some embodiments, the flashback pathway 56 may include the groove 58. In some embodiments, the groove 58 may include the notch 52. In these and other embodiments, the second proximal surface 48 may be extended to provide support to the tubular portion 38.

Figure 3C:
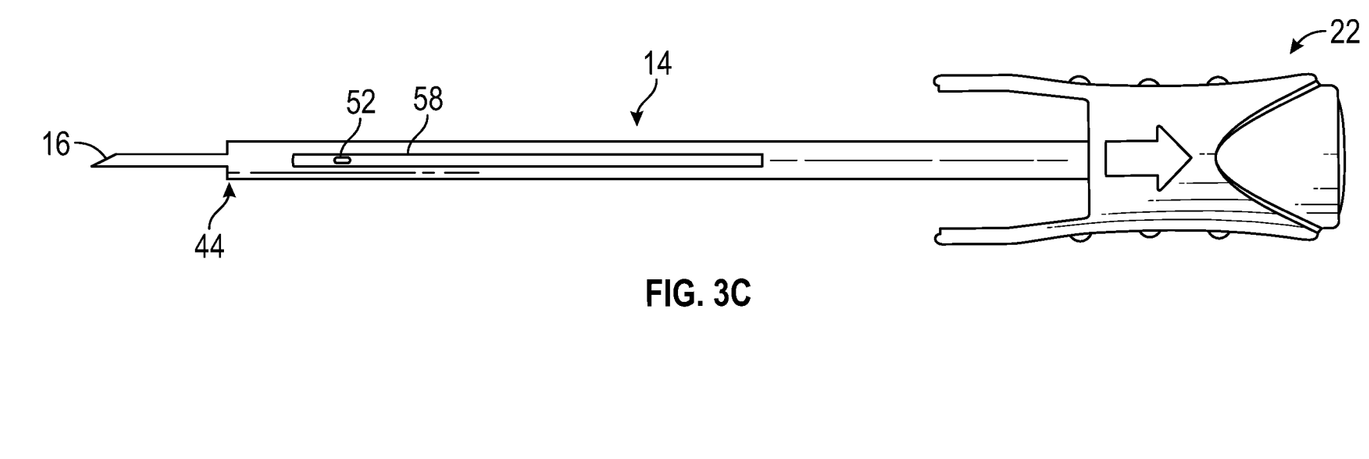
FIG. 3C is a top view of the introducer needle of FIG. 3A disposed within an example needle hub of the catheter system of FIG. 1A, according to some embodiments.
Figure 3D:
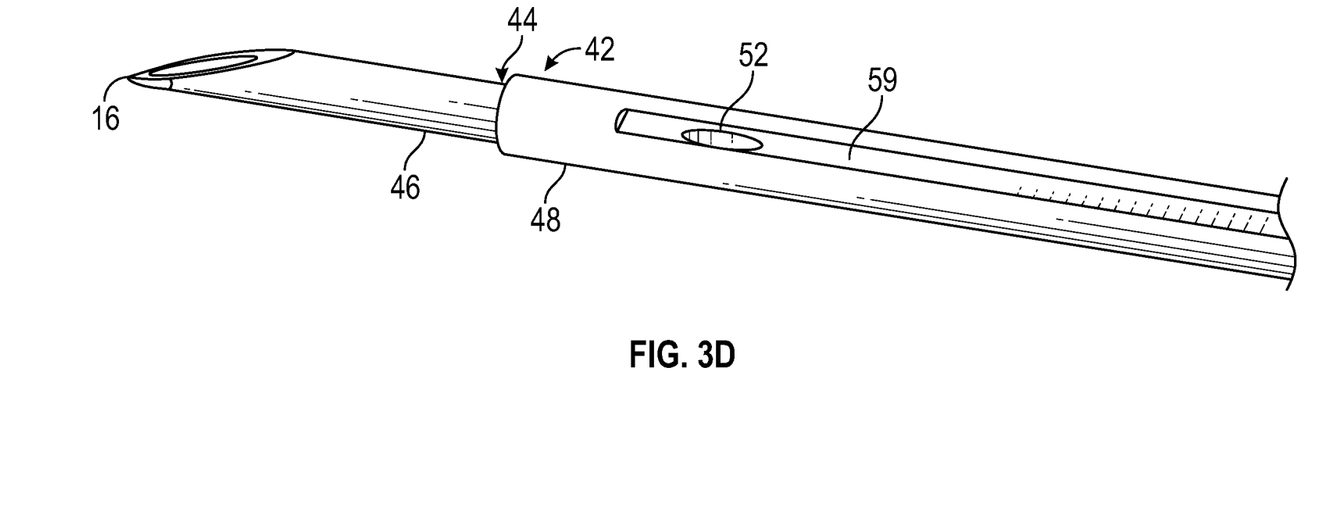
FIG. 3D is an upper perspective view of a distal end of another example introducer needle of the catheter system of FIG. 1A, according to some embodiments.

Referring now to FIG. 3C, the introducer needle 14 is illustrated removed from the catheter adapter 20, according to some embodiments. In some embodiments, the second proximal surface 48 may extend from the second transition surface 50 to a proximal end of the introducer needle 14 and/or the needle hub 22, which may provide strength to the introducer needle 14. In some embodiments, the second proximal surface 48 may extend from the second transition surface 50 along a portion of the introducer needle 14. In some embodiments, the groove 58 may extend along any length of the introducer needle 14. In some embodiments, a proximal end of the groove 58 may be disposed distal to the septum 24. In some embodiments, the second proximal surface 58 may extend through a proximal end of the catheter 12 when the introducer needle 14 is in the insertion position.

Referring now to FIG. 3D, an example flat portion 59 is illustrated. In some embodiments, the flat portion 59 may be similar to the groove 58 except that the flat portion 59 may not include walls. In some embodiments, a width of the flat portion 59 may be equal to a width of a cylinder forming the second proximal surface 48 at the location of the flat portion 59. In some embodiments, the cross-sectional view illustrated in FIG. 3B may also correspond to a cross-section view of the needle 14 of FIG. 3D disposed within the catheter 12 in the insertion position.

Figure 4A:
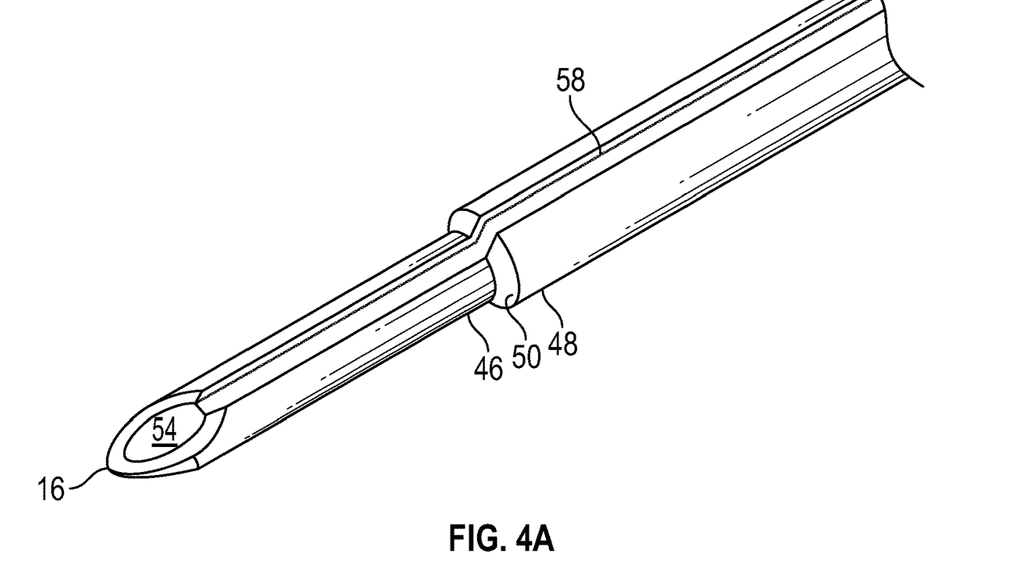
FIG. 4A is an upper perspective view of a distal end of another example introducer needle of the catheter system of FIG. 1A, according to some embodiments.
Figure 4B:
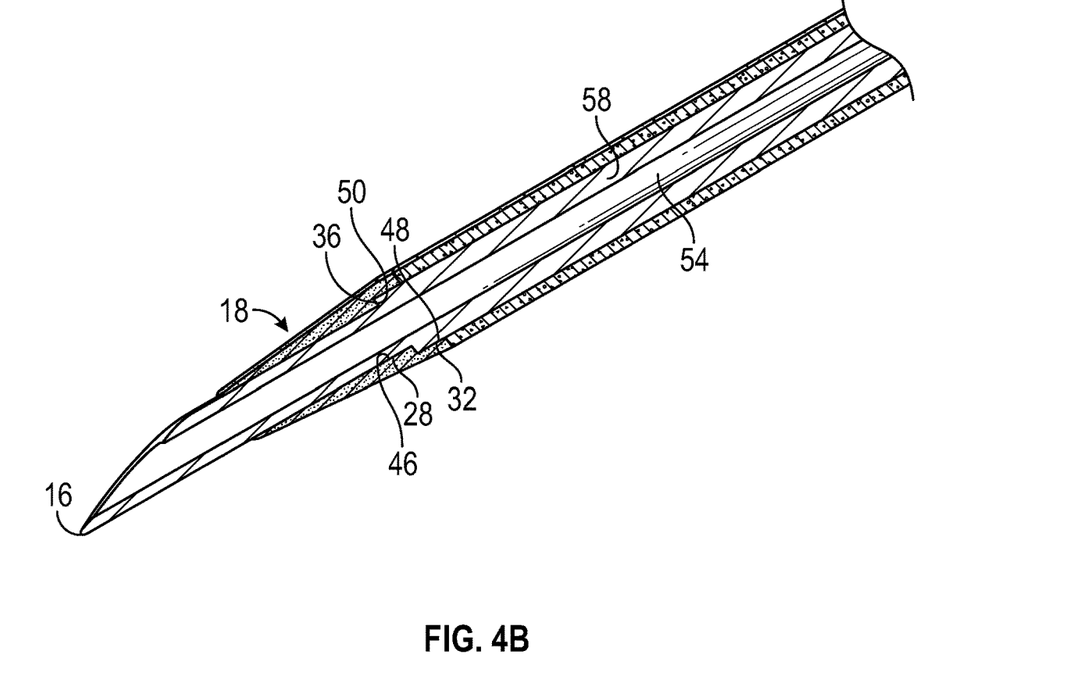
FIG. 4B is a cross-sectional view of the distal end of the introducer needle of FIG. 4A disposed in the insertion position within the catheter of FIG. 1B, according to some embodiments.

Referring now to FIGS. 4A-4B, in some embodiments, the groove 58 may extend through the second transition surface 50 and/or the second distal surface 46. In these and other embodiments, the groove 58 may extend through the distal tip 16 of the introducer needle 14 such that when the distal tip 16 is disposed within the vasculature of the patient, blood may flow directly into the groove 58 to provide flashback. As discussed with respect to FIG. 3, in some embodiments, the second proximal surface 48 may be extended to provide support to the tubular portion 38. In some embodiments, the groove 58 may extend along any length of the introducer needle 14. In some embodiments, a proximal end of the groove 58 may be disposed distal to the septum 24.

Figure 5A:
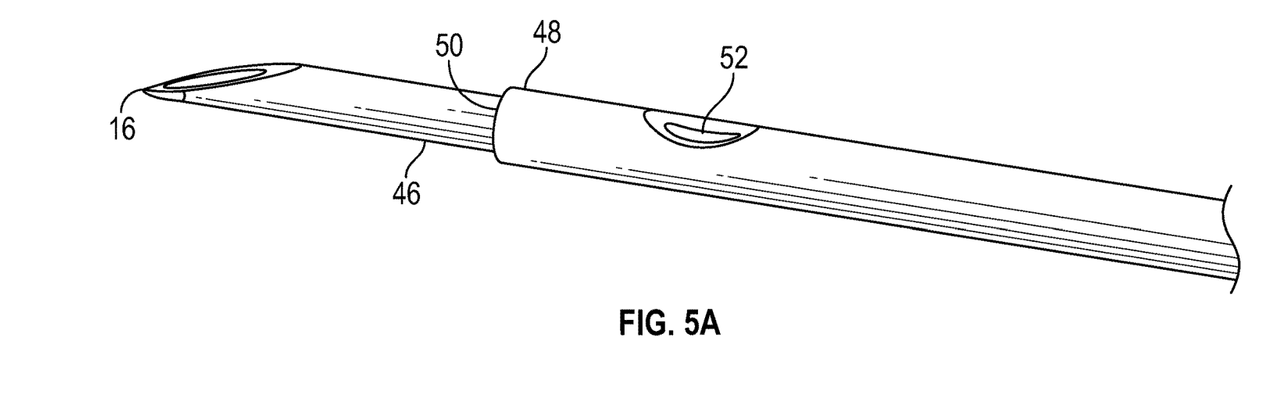
FIG. 5A is an upper perspective view of a distal end of another example introducer needle of the catheter system of FIG. 1A, according to some embodiments.
Figure 5B:
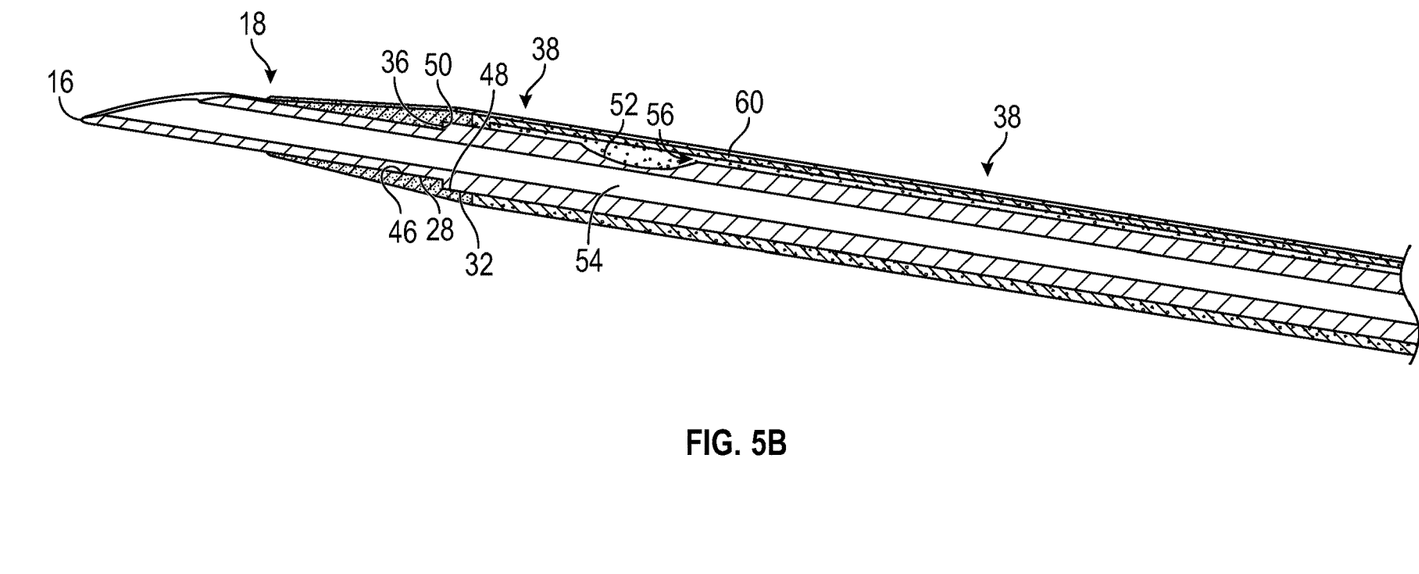
FIG. 5B is a cross-sectional view of the distal end of the introducer needle of FIG. 5A disposed in the insertion position within the catheter of FIG. 1B, according to some embodiments.
Figure 5C:
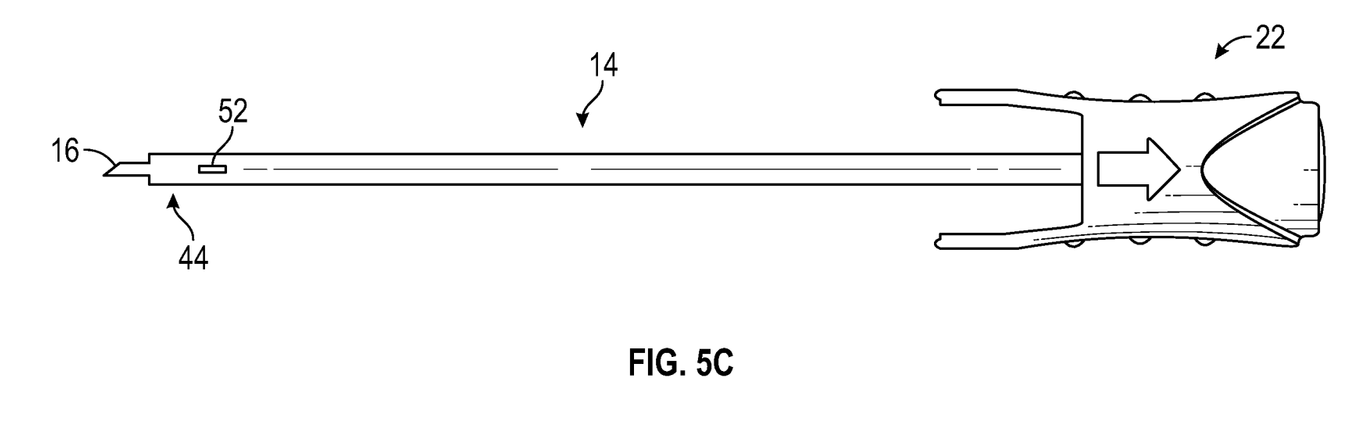
FIG. 5C is a top view of the introducer needle of FIG. 5A disposed within an example needle hub of the catheter system of FIG. 1A, according to some embodiments.

Referring now to FIGS. 5A-5B, in some embodiments, the second proximal surface 48 may include the notch 52, which may provide access to a needle lumen 54. In these and other embodiments, an inner surface of the tubular portion 38 may include an indent or channel 60, which may form the flashback pathway 56. In some embodiments, when the distal tip 16 is inserted into the vasculature of the patient, blood may flow through the distal tip 16, out of the notch 52, and into the channel 60 and may be visible to the user. As discussed with respect to FIGS. 3-4, in some embodiments, the second proximal surface 48 may be extended to provide support to the tubular portion 38. In some embodiments, the second proximal surface 48 may be smooth and generally uniform, as illustrated, for example, in FIG. 5A.

Figure 6:
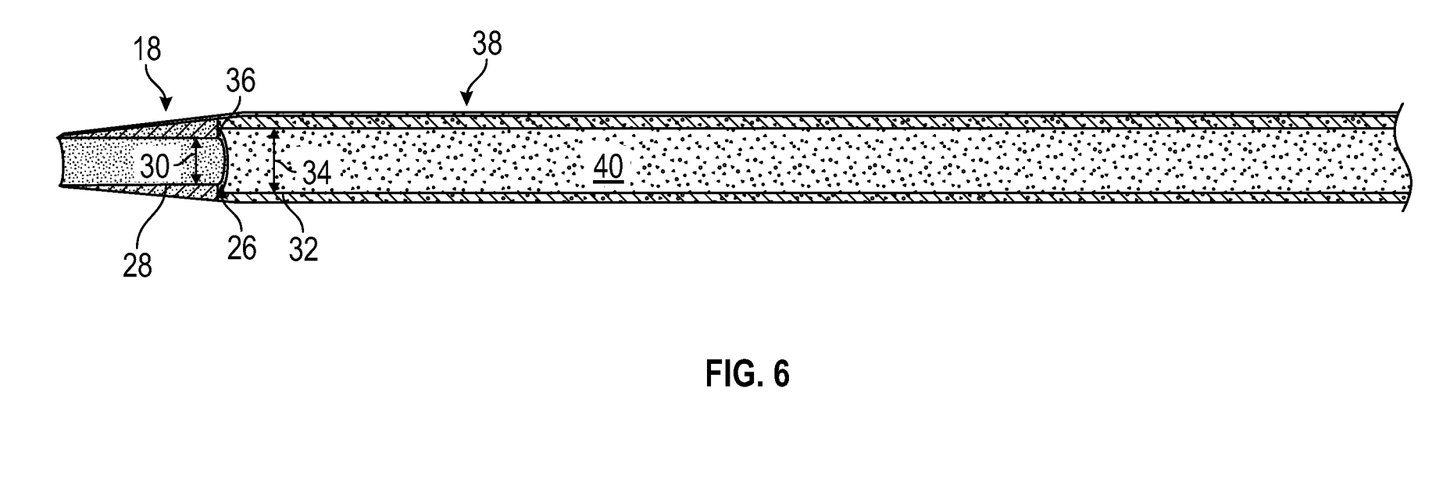
FIG. 6 is another cross-sectional view of the distal end of the catheter of FIG. 1B, according to some embodiments.

Referring now to FIG. 6, in some embodiments, the first distal surface 28 and the first transition surface 36 may be part of the distal tip 18 and thus constructed of the first material, while the first proximal surface 32 may be part of the tubular portion 38 and thus constructed of the second material. Accordingly, in some embodiments, the first transition surface 36 may be disposed proximate the second material. In some embodiments, the first distal surface 28, the first transition surface 36, and the first proximal surface 32 are part of the distal tip 18 and thus constructed of the first material, as illustrated, for example, in FIG. 1B.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope. All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:
1. A catheter assembly for insertion into vasculature of a patient, comprising,
   an over-the-needle catheter, comprising:
     a first annular stepped surface having a first distal surface with a first uniform inner diameter, a first proximal surface with a second uniform inner diameter greater than the first uniform inner diameter, and a first shoulder proximate the first proximal surface and disposed between the first distal surface and the first proximal surface and perpendicular to a longitudinal axis of the catheter assembly; and an elongate tubular portion proximate the first annular stepped surface and having the second uniform inner diameter of the first proximal surface, wherein the first shoulder, the first proximal surface, and the first distal surface are constructed of a first material with a harder durometer than a second material of the elongate tubular portion, the over-the- needle catheter having a catheter lumen extending therethrough, wherein the first annular stepped surface is disposed within the catheter lumen; and an introducer needle comprising a second annular stepped surface forming a distal end of a cylindrical needle feature, wherein the second annular stepped surface comprises a second distal surface, a second proximal surface, and a second shoulder disposed proximate the second proximal surface, between the second distal surface and the second proximal surface, and perpendicular to the longitudinal axis of the catheter assembly, wherein when the introducer needle is in an insertion position, the second distal surface contacts the first material of the first distal surface, the second proximal surface contacts the first material of the first proximal surface and the second material of the elongate tubular portion, and the second shoulder contacts the first material of the first shoulder such that proximal movement of the over-the-needle catheter relative to the introducer needle is inhibited.

2. The catheter assembly of claim 1, wherein an outer surface of the first distal surface, the first shoulder, and the first proximal surface is tapered.

3. The catheter assembly of claim 1, wherein the first material comprises a first plastic, wherein the second material comprises a second plastic.

4. The catheter assembly of claim 1, wherein the second proximal surface comprises a groove, wherein a distal end of the groove is spaced apart from the second shoulder, wherein a proximal end of the groove is disposed distal to a proximal end of the cylindrical needle feature, wherein the distal end of the groove contacts the second material.

5. The catheter assembly of claim 1, wherein the second proximal surface comprises a groove, wherein the groove extends through the second shoulder, through the second distal surface, and through a distal tip of the introducer needle.

6. The catheter assembly of claim 4, wherein the groove comprises a notch providing access to a needle lumen.

7. The catheter assembly of claim 1, wherein the introducer needle further comprises a notch disposed proximal to the cylindrical needle feature, the notch providing access to a needle lumen.

8. The catheter assembly of claim 1, wherein the second proximal surface and the cylindrical needle feature extend through a proximal end of the over-the-needle catheter when the introducer needle is in the insertion position with a sharp distal tip of the introducer needle disposed distal to the over-the-needle catheter.

9. The catheter assembly of claim 1, wherein the introducer needle further comprises a wall defining a needle lumen, wherein the second distal surface, the second shoulder, the second proximal surface, and the wall of the introducer needle are monolithically formed as a single unit.

10. The catheter assembly of claim 1, wherein the introducer needle further comprises a wall defining a needle lumen, wherein the cylindrical needle feature is bonded to the wall of the introducer needle to form the second shoulder and the second proximal surface.

11. The catheter system of claim 1, wherein the second material extends proximal to the cylindrical needle feature.

12. The catheter system of claim 4, further comprising a needle hub, wherein the cylindrical needle feature extends to the needle hub.

* * * * *